(12) United States Patent
Siltanen et al.

(10) Patent No.: US 7,269,241 B2
(45) Date of Patent: Sep. 11, 2007

(54) METHOD AND ARRANGEMENT FOR MEDICAL X-RAY IMAGING AND RECONSTRUCTION FROM SPARSE DATA

(75) Inventors: Samuli Siltanen, Helsinki (FI); Erkki Somersalo, Helsinki (FI); Ville Kolehmainen, Kuopio (FI); Matti Lassas, Helsinki (FI); Jari Kaipio, Kuopio (FI)

(73) Assignee: GE Healthcare Finland Oy, Helsinki (FI)

( * ) Notice: Subject to any disclaimer, the term of this patent is extended or adjusted under 35 U.S.C. 154(b) by 65 days.

(21) Appl. No.: 10/526,235

(22) PCT Filed: Aug. 27, 2003

(86) PCT No.: PCT/FI03/00625

§ 371 (c)(1),
(2), (4) Date: Aug. 30, 2005

(87) PCT Pub. No.: WO2004/019782

PCT Pub. Date: Mar. 11, 2004

(65) Prior Publication Data

US 2006/0104406 A1    May 18, 2006

(30) Foreign Application Priority Data

Aug. 28, 2002   (FI)   ................... 20021532

(51) Int. Cl.
*G01N 23/00*  (2006.01)

(52) U.S. Cl. .................. 378/4; 378/901; 382/131; 382/132

(58) Field of Classification Search ............. 378/4–20, 378/901; 382/131, 132
See application file for complete search history.

(56) References Cited

U.S. PATENT DOCUMENTS

2005/0105694 A1* 5/2005 Brandt ................ 378/210

FOREIGN PATENT DOCUMENTS

WO    WO-00/77719    12/2000

OTHER PUBLICATIONS

Reader et al., Fast Accurate Iterative Three-Dimensional Bayesian Reconstruction for Low-Statistics Positron Volume Rendering, IEEE Transactions on Nuclear Science, vol. 45, No. 3, Jun. 1998, pp. 1090-1095.*

(Continued)

*Primary Examiner*—Courtney Thomas
*Assistant Examiner*—Alexander Taningco
(74) *Attorney, Agent, or Firm*—Andrus, Sceales, Starke & Sawall, LLP (57) ABSTRACT

The invention relates to a medical X-ray device 5 arrangement for producing three-dimensional information of an object 4 in a medical X-ray imaging medical X-ray device arrangement comprising an X-ray source 2 for X-radiating the object from different directions and a detector 6 for detecting the X-radiation to form projection data of the object 4. The medical X-ray device 5 arrangement comprises:

means 15 for modelling the object 4 mathematically independently of X-ray imaging and means 15 for utilizing said projection data and said mathematical modelling of the object in Bayesian inversion based on Bayes' formula $$p(x|m) = \frac{p_{pr}(x)p(m|x)}{p(m)}$$

to produce three-dimensional information of the object, the prior distribution $p_{pr}(x)$ representing mathematical modelling of the object, the object image vector x, which comprise values of the X-ray attenuation coefficient inside the object, m representing projection data, the likelihood distribution p(m|x) representing the X-radiation attenuation model between the object image vector x and projection data m, p(m) being a normalization constant and the posteriori distribution p(x|m) representing the three-dimensional information of the object 4.

36 Claims, 9 Drawing Sheets

OTHER PUBLICATIONS

Morris et al., A Bayesian Approach to High Resolution 3D Surface Reconstruction from Multiple Images, Higher-Order Statistics, 1999, Proceedings of IEEE Signal Processing Workshop, Jun. 1999, pp. 140-143.*

Hybrid Interpolations to Enhance 3D Medical Image Reconstruction, Don-Lin Yang et al., Chinese Journal of Medical and Biological Engineering, Mar. 2000, ISSN 1019-0465 retrieved Nov. 17, 2003.

Total variation norm for three-dimensional iterative reconstruction in limited view angle tomography, M. Persson et al., Physics i Medicine and Biology, Mar. 2001, IOP Publishing U.K. ISSN 0031-9155, vol. 46, No. 3.

A Scale invariant Bayesian method to solve linear inverse problems, Mohammad-Djafari et al. presented at the 13th International Workshop on Maximum Entropy and Bayesian Methods (USA 1995, US2002/0015006 Abstract.

Three Dimensional Volumetric Modeling of the Internal Brain Structure Using Magnetic Resonance Imaging Slices, A. A. Sallam, et al., 2001 Proceedings of the 23rd Annual EMBS International Conference, Oct. 25-28, Istanbul, Turkey.

Reconstruction of 3-D Left Ventricular Motion from Planar Tagged Cardiac MR Images: An Estimation Theoretic Approach, Thomas S. Denney, Jr., et al. IEEE Transactions on Medical Imaging, vol. 14, No. 4, Dec. 1995.

* cited by examiner

Traditional tomosynthesis      Invention

FIGURE 9

METHOD AND ARRANGEMENT FOR MEDICAL X-RAY IMAGING AND RECONSTRUCTION FROM SPARSE DATA

CROSS REFERENCE TO RELATED APPLICATION

The present application is the U.S. national stage application of International Application PCT/FI2003/000625, filed Aug. 27, 2003, which international application was published on Mar. 11, 2004 as International Publication WO 2004/019782. The International Application claims priority of Finnish Patent Application 20021532, filed Aug. 28, 2002.

BACKGROUND OF THE INVENTION

Three-dimensional X-ray Imaging is based on taking several 1-D or 2-D projection images of a 3-D body from different directions. If 1-D projection images are available from all around a 2-D slice of the body with dense angular sampling, the inner structure of the slice can be determined. This is known as Computerized Tomography (CT) imaging technology, which is widely used in medicine today. A crucial part of CT technology is the reconstruction algorithm taking the X-ray images as argument and producing a voxel representation of the 3-D body.

In many practical cases X-ray projection Images are available only from a limited angle of view. A collection of X-ray images of a 3-D body is called sparse projection data if (a) the images are taken from a limited angle of view or (b) there are only a small number of images. Sparse projection data does not contain sufficient information to completely describe the 3-D body.

However, some a priori information about the body is typically available without X-ray imaging. Combining this information with sparse projection data enables more reliable 3-D reconstruction than is possible by using only the projection data.

Traditional reconstruction algorithms such as filtered backprojection (FBP), Fourier reconstruction (FR) or algebraic reconstruction technique (ART) do not give satisfactory reconstructions from sparse projection data. Reasons for this include requirement for dense full-angle sampling of data, difficulty to use a priori information for example nonnegativity of the X-ray attenuation coefficient and poor robustness against measurement noise. For example the FBP method relies on summing up noise elements with fine sampling, leading to unnecessarily high radiation dose.

BRIEF DESCRIPTION OF THE INVENTION

The aim of the invention is to overcome the problems met in 3-D reconstruction of the body that occur when using traditional reconstruction algorithms with sparse projection data. This is achieved by a method for producing three-dimensional information of an object in medical X-ray imaging in which method the object is modelled mathematically Independently of X-ray imaging. The object is X-radiated from at least two different directions and the said X-radiation is detected to form projection data of the object. Said projection data and said mathematical modelling of the object are utilized in Bayesian inversion based on Bayes' formula $$p(x|m) = \frac{p_{pr}(x)p(m|x)}{p(m)}$$

to produce three-dimensional information of the object, the prior distribution $p_{pr}(x)$ representing mathematical modelling of the object, x representing the object image vector, which comprises values of the X-ray attenuation coefficient inside the object, m representing projection data, the likelihood distribution p(m|x) representing the X-radiation attenuation model between the object image vector x and projection data m, p(m) being a normalization constant and the posteriori distribution p(x|m) representing the three-dimensional information of the object.

The invention also relates to a medical X-ray device arrangement for producing three-dimensional information of an object in a medical X-ray imaging, said medical X-ray device arrangement comprises:
means for modelling the object mathematically independently of X-ray imaging
an X-ray source for X-radiating the object from at least two different directions,
a detector for detecting the X-radiation to form projection data of the object,
and means for utilizing said projection data and said mathematical modelling of the object in Bayesian inversion based on Bayes' formula $$p(x|m) = \frac{p_{pr}(x)p(m|x)}{p(m)}$$

to produce three-dimensional information of the object, the prior distribution $p_{pr}(x)$ representing mathematical modelling of the object, x representing the object image vector, which comprises values of the X-ray attenuation coefficient inside the object, m representing projection data, the likelihood distribution p(m|x) representing the X-radiation attenuation model between the object image vector x and projection data m, p(m) being a normalization constant and the posteriori distribution p(x|m) representing the three-dimensional information of the object.

The invention is based on the fact that biological tissues have that kind of statistical a priori information that this information can be utilized successfully with bayesian inversion in medical x-ray imaging. The suitable a priori information makes it possible to model the biological tissue mathematically accurately enough and independently of X-ray imaging. From biological tissue it is possible to compile qualitative structural information which makes it possible to utilize the bayesian method successfully to solve the problems in medical three-dimensional x-ray imaging. There is a certain regularity in biological tissues and this regularity is useful especially with the bayesian method.

For example 10 x-ray images are taken from breasts of different persons. From these x-ray images is noticed that there is much similarity in the statistical structure of the breasts between different people. In other words biological tissues and x-ray images taken from the biological tissues have similar or almost similar statistical structure between different persons.

With Bayesian inversion it is possible to utilize a priori information efficiently in 3-D reconstruction from sparse projection data, because the suitable a priori information from the biological tissue makes possible to model the biological tissue mathematically accurately enough and independently of X-ray imaging. Any collection of projection data can be used in the reconstruction. Application-dependent a priori knowledge can be used to regularize the ill-posed reconstruction problem.

This invention improves the quality of 3-D reconstructions over traditional methods. In addition, the number of radiographs can be minimized without compromising quality of the reconstruction. This is very important in medical applications since the X-ray dose of the patient can be lowered.

DETAILED DESCRIPTION OF THE INVENTION

In practical imaging situations X-ray images are not always available from all around the body. The body might be visible only from certain directions due to imaging geometry. For example this is the case in 3-D mammography with the breast compressed against the detector, or in intraoral dental imaging with the detector inside the patient's mouth. This situation is called limited-angle tomography. Also, the region of interest might be surrounded by tissue that need not be imaged, like in extraoral dental imaging. This situation is called local tomography. In addition the number of radiographs should be minimized in medical applications for reducing the X-ray dose of the patient.

In the preferred embodiments of the invention Bayesian inversion algorithms are used to create a new type of 3-D medical X-ray imaging. It is intermediate between a projection radiograph and a full computed tomography scan. Two steps are needed to perform successfully such imaging: In step one, the doctor (a) collects all the prior information he or she has on the tissue of interest, and (b) takes the minimum number of radiographs containing the desired 3D information. In step two, a tomographic algorithm based on Bayesian inversion is used for 3D reconstruction. The algorithm contains two separate mathematical models. First, all a priori information (i.e. information that is independent of X-ray imaging) is used to model the unknown object mathematically. The model is put into the form of prior distribution in Bayes' formula. Second, the measurement is modelled mathematically. This involves the geometry of the imaging device, position of the detector and X-ray source during the exposure of each projection image and a model for X-ray attenuation inside tissue. The mathematical model of the measurement is put into the form of likelihood distribution in Bayes' formula.

Figure 1:
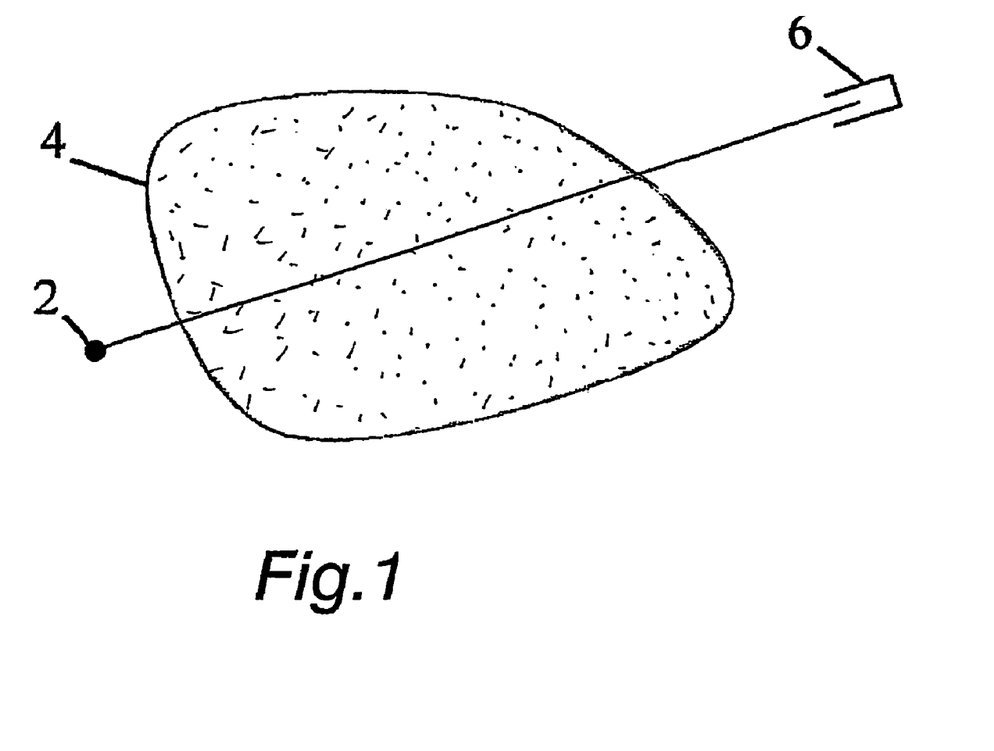
FIG. 1 shows a simple example of X-ray imaging.

In FIG. 1 is shown a simple example of X-ray imaging, where an X-ray source 2 is placed on one side of an object 4 under imaging. Radiation passes through the object and is detected by a detector 6 on the other side. The X-ray source is for example a X-ray source of an intraoral X-ray source of a dentist, of a dental panoramic X-ray device, of a surgical C-arm X-ray device, of a mammography device or of any other medical X-ray device and the detector 6 is a detector of some of those devices. Usually the detector 6 is a digital sensor that can be thought of as a 2-D array of almost pointlike detectors.

The 3-D body under imaging is modelled by nonnegative X-ray attenuation coefficient. The value gives the relative intensity loss of the X-ray travelling within a small distance dr:

$$\frac{dI}{I} = -x(r)dr \qquad (1)$$

The X-radiation has initial intensity $I_0$ when entering the object 4 and a smaller intensity $I_1$ when exiting the object. The following equation shows the attenuation law:

$$\int_L x(r)\,dr = -\int_L \frac{I'(r)}{I(r)}\,dr = \log I_0 - \log I_1 \qquad (2)$$

where initial intensity $I_0$ is known by calibration, and intensity after object $I_1$ is known from the corresponding point value in a projection image. Thus the measured data is the integral of x along the line L.

In the above model it is not taken into account (a) scattering phenomena resulting in X-rays changing their direction, or (b) the dependency of attenuation on the X-ray spectrum resulting in low-energy photons being more easily attenuated than high-energy ones. Effect (b) causes errors in measurements and is sometimes referred to as beam hardening. More detailed models can be utilized in Bayesian inversion to overcome (a) and (b).

Figure 2A:
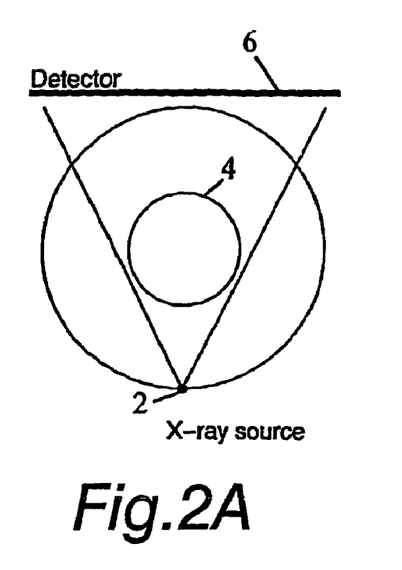
FIGS. 2A -2B show a difference between global tomography and local tomography.
Figure 2B:
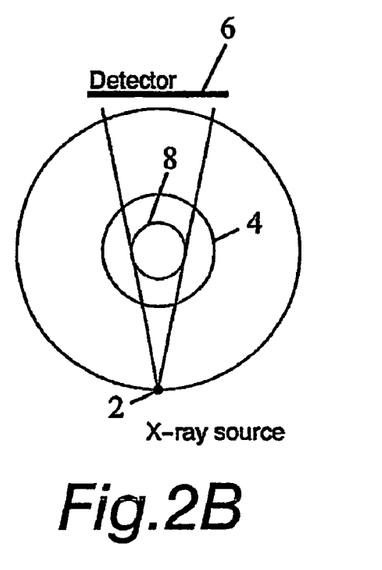
Figure 3A:
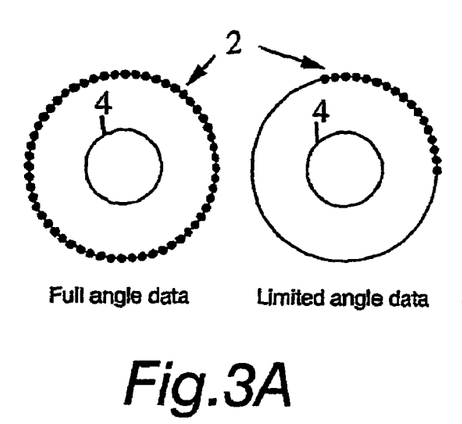
FIGS. 3A-3B show different types of sparse projection data. Every black dot represents a location of the X-ray source for taking one projection image.
Figure 3B:
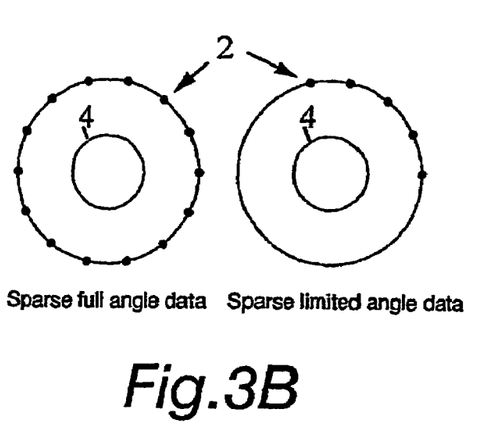

In medical imaging the geometrical arrangements of the X-ray source and digital sensor vary according to the diagnostic task and equipment. FIGS. 2A-2B and 3 illustrate the types of tomographic data resulting from different imaging situations. For clarity, here are presented two-dimensional examples; similar situations can be considered in 3-D.

In FIG. 2A-2B are shown two cases according to whether the whole object 4 is fully visible in each projection or not. These cases are called global tomography and local tomography, respectively. In FIG. 2B is radiated only ROI (Region Of Interest) 8.

The types of data described in FIGS. 3A-3B cover a large range of specific imaging tasks. The choice of data collection dictates what kind of features and details it is easiest to reconstruct reliably from the data. Thus the choice of projection views must be made according to the diagnostic task at hand. In traditional CT imaging, projections are taken from all around the object 4. In the preferred embodiments of the invention radiation dose is lowered by sampling the angular variable more sparsely. FIG. 3A presents more dense angular data with full angle and limited angle measurements. FIG. 3B presents more sparse angular data, also with full and limited angles of measurement.

Figure 4A:
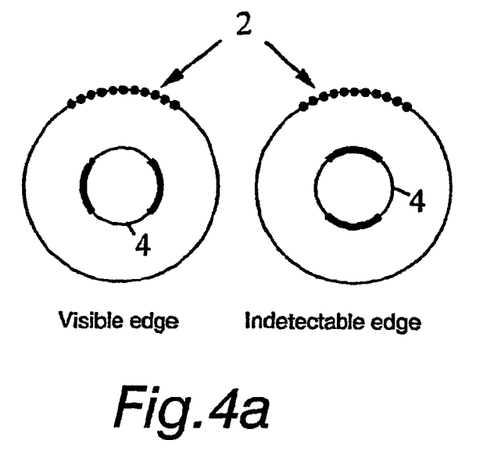
FIGS. 4A-4B show examples of parts of boundaries and cracks of an object visible and invisible without a priori information.
Figure 4B:
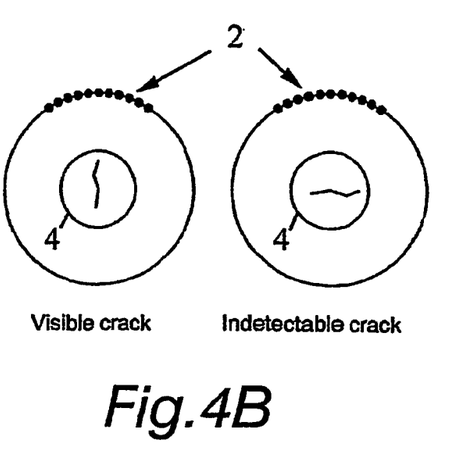

In FIGS. 4A and 4B there are presented examples of parts of boundary and cracks that are visible or undetectable in reconstruction without a priori information. In FIG. 4A there is an object 4 under imaging with an edge on the surface of the object. The edge is detectable on the leftmost position where the edge is more parallel to the direction of the X-rays. In the FIG. 4B there is a crack inside of the object 4. The crack is detectable in the leftmost position parallel to the angle of measurement.

The main idea in Bayesian inversion method is to consider the inverse problem as a problem of statistical inference. All variables are redefined to be random variables. The randomness reflects uncertainty of their actual values and the degree of uncertainty is coded in the probability distributions of these random variables.

When modelling the measurement mathematically the X-ray attenuation model and the observation can be assumed linear. The model Is presented in the following equation.

$$m=Ax+e, \quad (3)$$

where the variables m, x and e are random variables.

Figure 5:
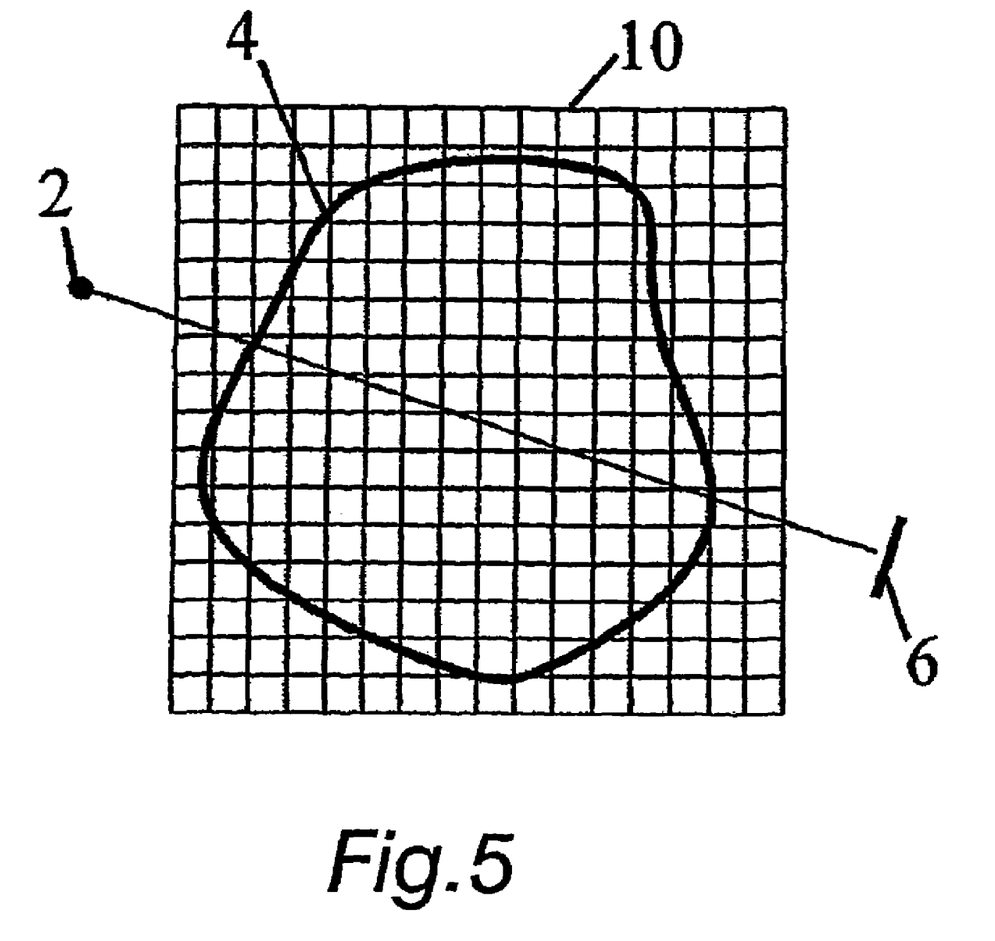
FIG. 5 illustrates "pencil beam" X-ray attenuation model.

The matrix A comes from the pencil beam model for the X-ray attenuation. This is presented in FIG. 5. There the unknown 3-D body of the object 4 is divided into small voxels 10, and the matrix A contains the lengths of the path of the X-ray inside each voxel. In this way the integral in formula (2) is approximated with a simple numerical quadrature.

Assume now that the object image vector x and the noise are jointly independent random variables. The conditional probability distribution of x given the measurement m is given by Bayes' formula in the form $$p(x|m) = \frac{p_{pr}(x)p_{noise}(m-Ax)}{p(m)}, \quad (4)$$

where p(m) is a normalization constant. The density p(x|m) is called the posteriori distribution of x. $p_{noise}(m-Ax)=p(m|x)$ is a likelihood distribution representing the X-radiation attenuation model between the object image vector x and projection data m.

The density $P_{pr}$, called the prior distribution of x, is designed to contain all possible information available of the actual object 4 independently of X-ray imaging. It is crucial, in contrast to several classical regularization methods, that the choice of the prior distribution should not be based on the projection data. The rule of thumb in the design of prior distributions is that typical image vectors (say, of some existing library) should have high prior probability while atypical or impossible ones should have low or negligible probability.

In the framework of the Bayesian inversion theory, the posterior distribution in formula (4) represents the complete solution of the 3D reconstruction problem.

To produce an image of the object 4 based on the posterior distribution, several alternatives exist. The most common ones are the maximum a posteriori estimator (MAP) and conditional mean estimator (CM). They are defined by the formulas $$p(xMAP|m)=\max p(x|m), \quad (5)$$

where the maximum on the right hand side is taken over all x, and $$xCM=\int xp(x|m)dx. \quad (6)$$

Finding the MAP estimator is an optimization problem while finding the CM estimator is a problem of integration.

Figure 6:
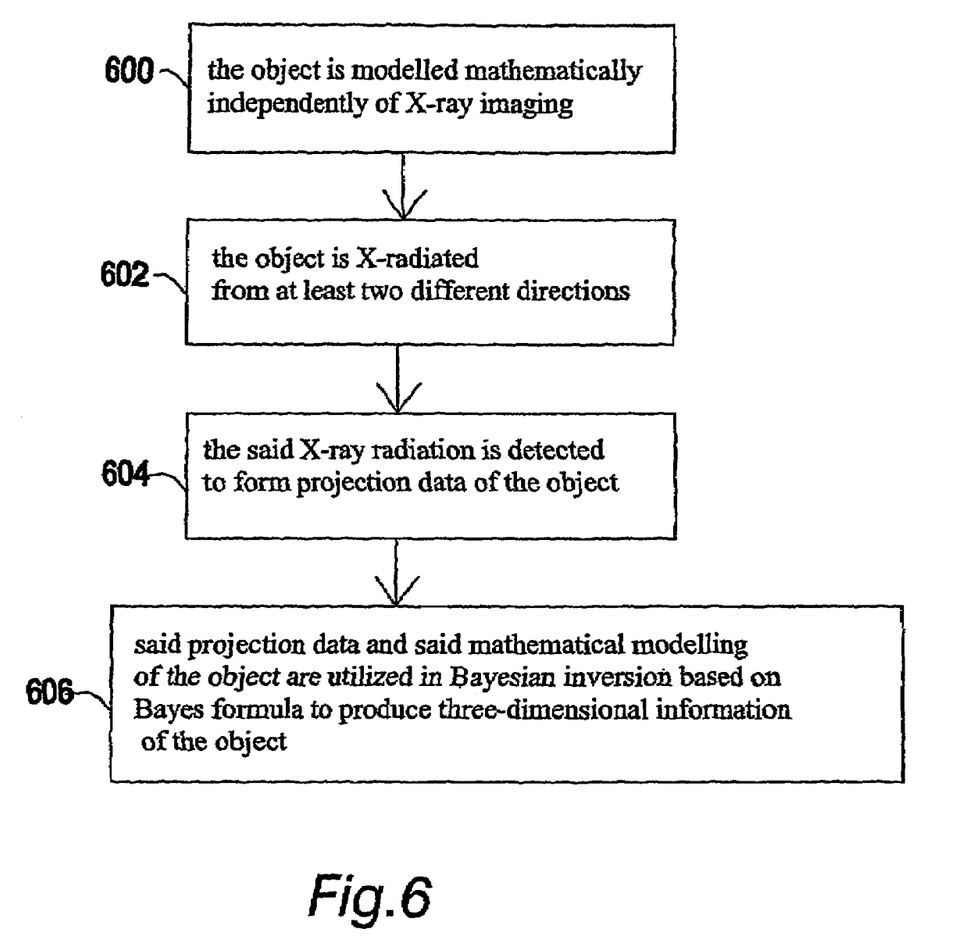
FIG. 6 is basic flow chart of the method according to the invention.

In FIG. 6 is presented a basic flow chart of the method according to the invention. In method step 600 the object is modelled mathematically independently of X-ray imaging. In method step 602 the object is X-radiated from at least two different directions. In method step 604 the said X-radiation is detected to form projection data of the object. In method step 606 said projection data and said mathematical modelling of the object are utilized in Bayesian inversion based on Bayes formula to produce three-dimensional information of the object. The method step 600 is also possible to perform after method step 602 or 604.

In the first preferred embodiment of the invention is presented an application to dental radiology.

X-ray projection images are conventionally used in dental radiology. However, certain diagnostic tasks require more precise knowledge of the 3D structure of tissue than is available in two-dimensional radiographs. Such tasks include implant planning and detection of bone loss between tooth roots.

Figure 7:
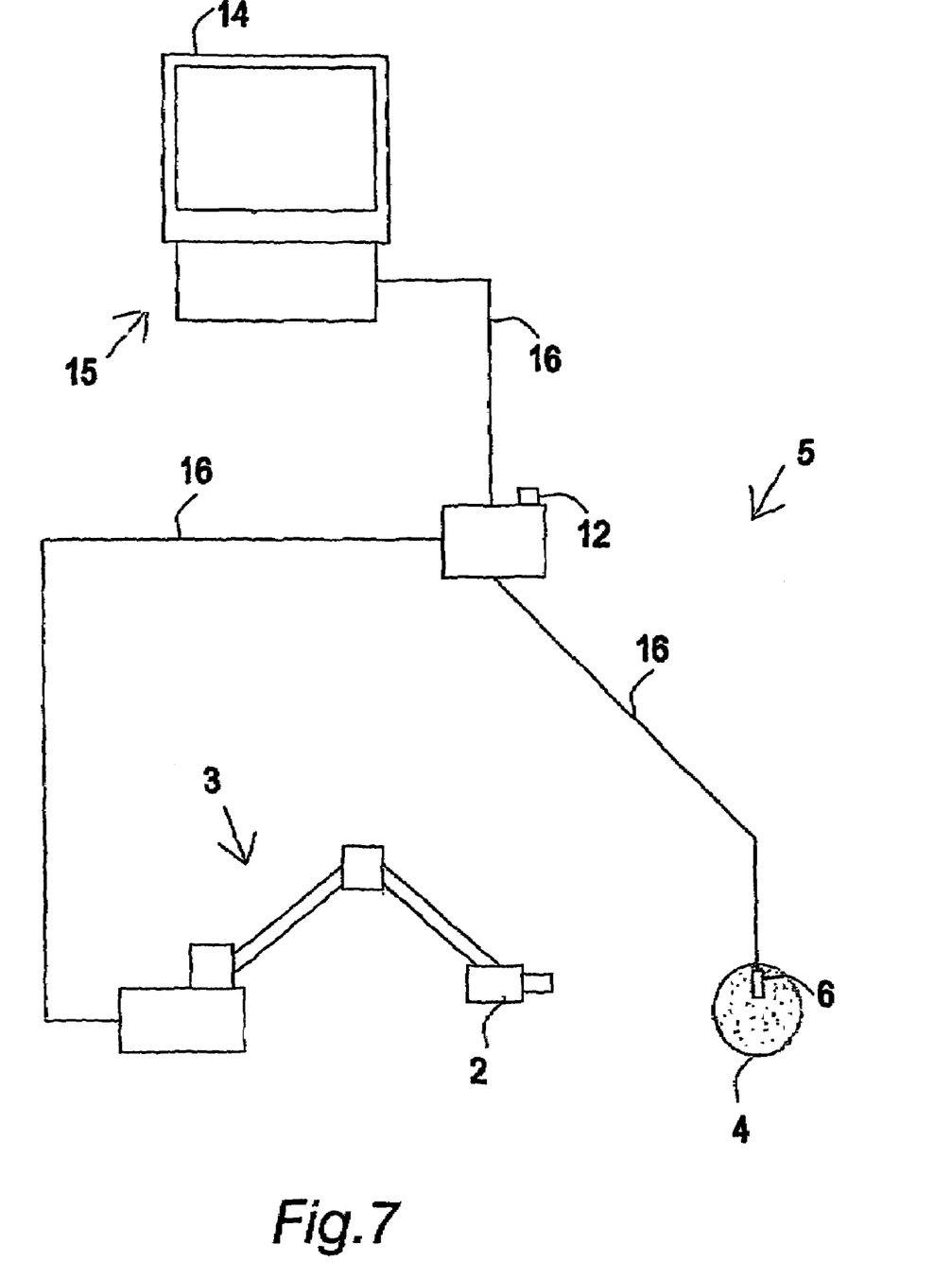
FIG. 7 is an intraoral X-ray device arrangement presenting one preferred embodiment of the invention.

In FIG. 7 is presented an intraoral X-ray device 5 arrangement presenting the first preferred embodiment of the invention. It is important to notice that this is only an example of the medical X-ray device 5 arrangement where the invention is possible to be utilized.

The medical x-ray device 5 in the preferred embodiments of the invention is for example a dental panoramic X-ray device, a surgical C-arm X-ray device or a mammography device.

In the first preferred embodiment of the invention the articulated arm arrangement 3 moves the X-ray source 2 to the right position. The X-radiation begins by pressing the exposure button 12. The X-ray source 2 X-radiates the object 4, which is for example teeth of a patient. The detector 6 detects the X-radiation. The image information which is got by detecting the X-radiation is sent by communication link 16 to the computer 14. The computer comprises the software means 15 to process the image information according to the invention. There can be more than one computer 14 and also the software means 15 can be situated in more than one computer 14. For example the first computer 14 is a computer which is used in x-ray imaging. The second computer 14 is a computer which is used in processing the image information according to the invention. It is possible to have the second computer 14 far away from the actual medical x-ray device 5. For simplicity in FIG. 7 is shown only one computer 14.

In the first preferred embodiment (FIG. 7) of the invention, the dentist's X-ray equipment is used for taking a set of 2D projection images that are used as input for Bayesian 3D reconstruction algorithm. Such equipment includes an intraoral X-ray unit and a digital intraoral sensor.

Benefits of this approach over conventional CT scan are
low cost and convenient usage,
high resolution of the projection images,
possibility to take as few radiographs as is needed to capture the relevant 3D information, minimizing radiation dose to the patient,
the possibility to choose imaging directions so that the X-rays do not pass through the whole head but only the interesting tissue, further reducing dose.

In the preferred embodiments of the invention, Bayesian inversion is used for the 3D reconstruction. Input data for the algorithm is the set of projection images and the following a priori knowledge:
(a) Dental tissue consists of few approximately homogeneous regions with well-defined boundaries.
(b) Dental tissue can only attenuate X-radiation, not intensify it.

The example of the detector 6 used in the first preferred embodiment of the invention is based on charge coupled device (CCD) technology and has dynamic range of 4096 gray levels. The size of the active imaging area is 34 mm*26 mm and the resolution is 872*664 pixels. After exposure, each pixel contains an integer which is proportional to the number of X-ray quanta that hit the pixel's area.

Alternative detectors include any other digital intraoral sensor, digitized X-ray film, or any intraoral sensing device converting detected X-ray photons to a digital image.

Figure 8:
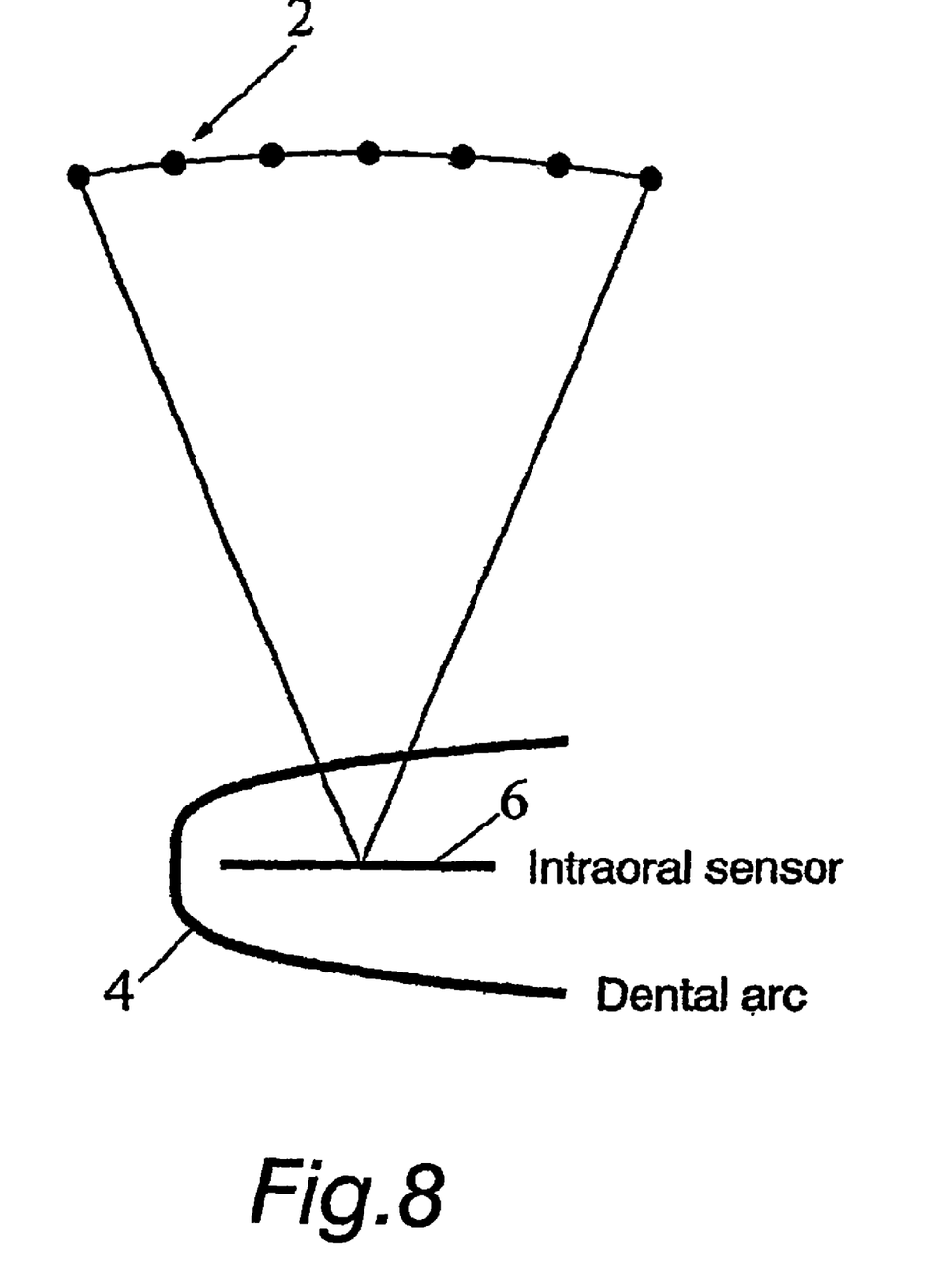
FIG. 8 shows a measurement geometry of dental limited-angle tomography with a digital intraoral sensor.

In the measurement geometry the focal point of the X-ray source 2 moves horizontally on a circle in the plane 10, with center at the detector 6, see FIG. 8. In FIG. 8, the detector 6 corresponds to one row of CCD pixels in the CCD sensor.

In FIG. 8 is presented an example of taking seven radiographs of some teeth of a patient. The total opening angle of the projection views is 55 degrees in this example. FIG. 8 represents the xy plane, and the z-coordinate axis is thought to be perpendicular to the plane of the paper.

In the preferred embodiments, mathematical modelling of the object 4 can be done with a prior distribution of the form in formula (7):

$$p_{pr}(x) = \exp\left(-\alpha \sum_{N} U_N(x)\right) \quad (7)$$

where the sum is taken over a collection of 3D neighbourhoods N and the value $U_N(x)$ depends only on the values of voxels belonging to the neighborhood N, and α is a positive regularization parameter used to tune the width of the prior distribution. The neighborhood N is typically a set of voxels whose center points are doser to each other than some predefined maximum distance.

It is to be noted that formula (7) does not define a probability distribution since it does not integrate to 1. Instead, the integral diverges. However, when used in the Bayes formula (4) with a suitable likelihood distribution, the posterior distribution is integrable. The same remark concerns the prior distributions derived from (7), that is, formulae (9), (10) and (11).

In the preferred embodiments of the invention the three-dimensional problem can be reduced to a stack of two-dimensional problems each corresponding to a plane determined by a constant value of z. Here FIG. 8 represents exactly the situation in the xy plane, i.e. the plane z=0. Each row in the detector corresponds to one such 2D problem. This approach leads to small approximation error because the X-ray source does not move in the correct plane for nonzero z, and this error is neglected.

Next the modelling of a 2D tomographic problem is explained. Let $$m(j) = A \, x(j) + e(j) \quad (8)$$

denote the jth 2D tomographic problem. Here the vector m(j) contains the readings on jth row from each of the seven radiographs. The vector x(j) is the jth slice of the 3-D representation x of the object 4 under imaging. The matrix A is the pencil beam model matrix for the 2-D tomography problem.

Now x(j) is a 2D array of pixels. The pixels are denoted by x(j)[k,q], where k=1,2, . . . ,K is row index and q=1,2, . . . ,Q is column index.

The mathematical modelling of the object 4, i.e. incorporation of prior information, is next explained for the 2D slice. Define $$p_{pr}(x^{(j)}) = \exp\left(-\alpha \sum_{k=1}^{K} \sum_{q=1}^{Q} U(N(x^{(j)}[k, q]))\right) \quad (9)$$

where the value U(N(x(j)[k,q])) depends only on the values of pixels belonging to the neighborhood N of the pixel x(j)[k,q], the constant c is a normalization constant and a is a positive regularization parameter used to tune the width of the prior distribution. The choice of the neighborhoods N(x(j)[k,q]) is arbitrary, but a typical choice is the set of pixels whose centerpoints are doser to the centerpoint of x(j)[k,q] than some predefined distance.

In the preferred embodiment, the neighborhoods are chosen to consist of two adjacent pixels. Further, the function U is chosen to be a power of absolute value of the difference between adjacent pixels. These choices lead to formula (10):

$$p_{pr}(x^{(j)}) = \exp\left(-\alpha\left(\sum_{k=1}^{K-1} \sum_{q=1}^{Q} |x^{(j)}[k, q] - x^{(j)}[k+1, q]|^s + \sum_{k=1}^{K} \sum_{q=1}^{Q-1} |x^{(j)}[k, q] - x^{(j)}[k, q+1]|^s\right)\right) \quad (10)$$

where s is a positive real number, and α is a regularization parameter used to tune the width of the prior distribution.

In the equation (11) is presented non-normalized total variation (TV) distribution, when s=1 in equation (10). This is the case according to the preferred embodiment of the invention, because when s=1 the prior model becomes such that it gives high probability for objects consisting of a few areas of different attenuation with well-defined boundaries.

$$prTV(x^{(j)}) = \exp\left(-\alpha\left(\sum_{k=1}^{K-1} \sum_{q=1}^{Q} |x^{(j)}[k, q] - x^{(j)}[k+1, q]| + \sum_{k=1}^{K} \sum_{q=1}^{Q-1} |x^{(j)}[k, q] - x^{(j)}[k, q+1]|\right)\right) \quad (11)$$

X-radiation can only attenuate, not strengthen, inside tissue. This leads to positivity prior pos defined by pos(x(j))=1 if all pixels of x(j) are positive, 0 otherwise. (12)

The explanation of modeling of one 2D tomographic problem is now complete.

The stack of 2D problems are connected to each other by demanding that consecutive 2D slices x(j) and x(j−1) should not be very different. Mathematically this Is expressed as follows:

$$pr3D(x(j)) = \exp(-\gamma \Sigma\Sigma |x(j)[k,q] - x(j-1)[k,q]|), \quad (13)$$

where the sums are taken over k=1, . . . ,K and q=1, . . . ,Q and γ>0 is another regularization parameter. So the prior distribution in formula (4) is the product of (11), (12) and (13):

$$p_{pr}(x(j)) = prTV(x(j))pos(x(j))pr3D(x(j)). \quad (14)$$

The measurements are taken into account in the form of the likelihood distribution $$p(m^{(j)} | x^{(j)}) = c\exp\left\{-\frac{1}{2}(m^{(j)} - Ax^{(j)})^T \sum^{-1} (m^{(j)} - Ax^{(j)})\right\} \quad (15)$$

where $\Sigma$ is the covariance matrix of the Gaussian noise vector e. c is a normalization constant.

In reality, X-radiation measurement noise is Poisson distributed. Formula 15 uses a Gaussian approximation to the Poisson distribution.

All the parts are presented of the right hand side of (4). Next it is looked for the MAP estimate of x(j), that is, the image x(j) that gives the largest value for the posteriori distribution (4). This is equivalent to finding the image x(j) that minimizes the expression $$F(x^{(j)}) = \frac{1}{2}(m^{(j)} - Ax^{(j)})^T \sum^{-1} (m^{(j)} - Ax^{(j)}) + \quad (16)$$
$$-\log(prTV(x^{(j)})) - \log(pr3D(x^{(j)}))$$

with the additional requirement that every pixel of x(j) is positive.

Figure 9:
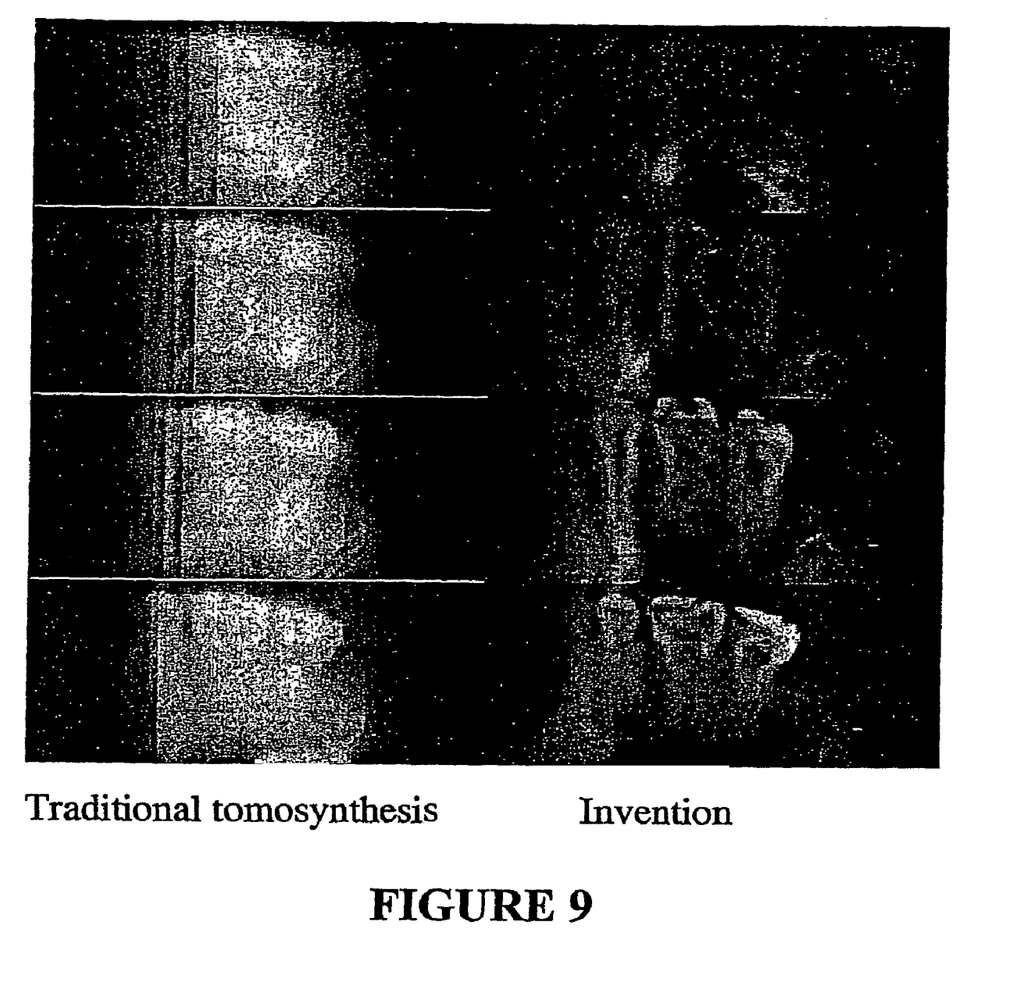
FIG. 9 shows results of 3D reconstruction of head phantom in the first preferred embodiment.

Minimization of (16) is difficult since F is not a differentiable function due to the absolute values present in (11) and (13) and due to the sharp cutting in (12). The absolute values in (11) and (13) are replaced by $$|t| \approx h_\beta(t) = \frac{1}{\beta}\log(\cosh(\beta t)), \quad (17)$$

where $\beta>0$, enabling the use of efficient gradient-based minimization routines. The positivity constraint is taken care of by an interior search minimization method. The results are shown in FIG. 9 in comparison with traditional tomosynthesis technique based on backprojection.

In this description explained mathematic modelling and other image information processing are performed by software means 15 to accomplish three-dimensional information of the object 4.

In the second preferred embodiment the invention is utilized in dental panoramic x-ray imaging. The object 4 is typically teeth of the patient and the medical x-ray device 5 arrangement is dental panoramic x-ray device arrangement.

In the third preferred embodiment the invention is utilized in mammography, for example in FFDM (Full Field Digital Mammography). There the object 4 is breast of human being and the medical x-ray device 5 arrangement is mammography device arrangement.

In the fourth preferred embodiment the invention is utilized in surgical x-ray imaging. There the object 4 is the body part under surgery and the medical x-ray device 5 arrangement is surgical x-ray device arrangement.

In the first, second, third and fourth preferred embodiments of the invention the basic method steps are same as mentioned with the flow chart in FIG. 6. The utilizing of the invention in the second, third and fourth preferred embodiment is similar to what is described with the first preferred embodiment of the invention and elsewhere in this application except for different medical x-ray imaging applications and their differences because of different medical x-ray devices and different objects to be x-ray imaged.

Although the invention is described above with reference to the examples illustrated in the attached figures, it is to be understood that the invention is not limited thereto but can be varied in many ways within the inventive idea disclosed in the attached claims.

The invention claimed is:

1. A method for producing three-dimensional information of an object in medical X-ray imaging, characterized in that
   the object is modelled mathematically independently of X-ray imaging,
   the object is X-radiated from at least two different directions and the said X-radiation is detected to form projection data of the object,
   said projection data and said mathematical modelling of the object are utilized in Bayesian inversion based on Bayes' formula $$p(x|m) = \frac{p_{pr}(x)p(m|x)}{p(m)}$$

the prior distribution $p_{pr}(x)$ representing mathematical modelling of the object, x representing the object image vector, which comprises values of the X-ray attenuation coefficient inside the object, m representing projection data, the likelihood distribution p(m|x) representing the X-radiation attenuation model between the object image vector x and projection data m, p(m) being a normalization constant and the posteriori distribution p(x|m) representing the three-dimensional information of the object, and
three-dimensional medical X-ray imaging information of the object is produced.

2. A method according to claim 1, characterized in that the three-dimensional information of the object is one or more two-dimensional images representing X-ray attenuation coefficient along slices through the object.

3. A method according to claim 1, characterized in that the three-dimensional information of the object is a three-dimensional voxel representation of the X-ray attenuation in the object.

4. A method according to claim 1, characterized in that a measurement model is m=Ax+e, where matrix A contains the lengths of the path of the X-ray inside each voxel and the noise e is independent of object image vector x leading to the likelihood distribution $$p(m|x) = p_{noise}(m - Ax).$$

5. A method according to claim 1, characterized in that the said mathematical modelling employs the fact that X-radiation attenuates when passing through the object, which means that every image voxel is nonnegative.

6. A method according to claim 1, characterized in that mathematical modelling is expressed by the formula:

$$p_{pr}(x) = \exp\left(-\alpha \sum_N U_N(x)\right)$$

where the sum is taken over a collection of 3D neighbourhoods N and the value $U_N(x)$ depends only on the values of voxels belonging to the neighborhood N, and $\alpha$ is a positive regularization parameter used to tune the width of the prior distribution.

7. A method according to claim 1, characterized in that a 3D tomographic problem is divided into a stack of 2D tomographic problems and in every such 2D problem, the mathematical modelling is expressed by the formula:

$$p_{pr}(x) = \exp\left(-\alpha \sum_N U_N(x)\right)$$

where the sum is taken over a collection of 2D neighbourhoods N and the value $U_N(x)$ depends only on the values of pixels belonging to the neighborhood N, and $\alpha$ is a positive regularization parameter used to tune the width of the prior distribution, and the 2D tomographic problems are related to each other by the formula $$pr3D(x(j)) = \exp(-\gamma \Sigma\Sigma |x(j)[k,q] - x(j-1)[k,q]|),$$

where the sums are taken over all pixels (k=1, ..., K, q=1, ..., Q) and $\gamma>0$ is another regularization parameter.

8. A method according to claim 7, characterized in that the neighborhoods comprise two adjacent pixels and U calculates a power of the absolute value of the difference, leading to the formula $$p_{pr}(x^{(j)}) = \exp\left(-\alpha\left(\sum_{k=1}^{K-1}\sum_{q=1}^{Q} |x^{(j)}[k,q] - x^{(j)}[k+1,q]|^s + + \sum_{k=1}^{K}\sum_{q=1}^{Q-1} |x^{(j)}[k,q] - x^{(j)}[k,q+1]|^s\right)\right)$$

where s is a positive real number.

9. A method according to claim 8, characterized in that s=1 which corresponds to total variation (TV) distribution for prior describing objects comprised of different regions with well-defined boundaries.

10. A method according to claim 1, characterized in that mathematical modelling is qualitative structural information of the target where the structural information is encoded in prior distributions that are concentrated around object image vectors x that correspond to the physiological structures of the object.

11. A method according to claim 1, characterized in that the mathematical modelling comprises a list or probability distribution of possible attenuation coefficient values in the object.

12. A method according to claim 1, characterized in that the X-ray imaging geometry, such as X-ray source position, has unknown error modelled in the distribution p(m|x).

13. A method according to claim 1, characterized in that the X-radiation measurement noise is Poisson distributed.

14. A method according to claim 1, characterized in that the medical X-ray imaging is dental radiography.

15. A method according to claim 1, characterized in that the medical X-ray imaging is surgical C-arm imaging.

16. A method according to claim 1, characterized in that the medical X-ray imaging is mammography.

17. A method according to claim 1, characterized in that three-dimensional information of the object is produced on the basis of a maximum a posteriori estimator (MAP) which is calculated by the equation:

$$p(X_{MAP}|m) = \max p(x|m)$$

m representing projection data and x representing the object image vector and where the maximum on the right hand side of the equation is taken over all x.

18. A method according to claim 1, characterized in that three-dimensional information of the object is produced on the basis a conditional mean estimator (CM), which is calculated by the equation:

$$X_{CM} = \int x p(x|m) dx$$

where m represents projection data and x represents the object image vector.

19. A medical X-ray device arrangement for producing three-dimensional information of an object in a medical X-ray imaging, characterized in that the medical X-ray device arrangement comprises:
 means for modelling the object mathematically independently of X-ray imaging
 an X-ray source for X-radiating the object from at least two different directions
 a detector for detecting the X-radiation to form projection data of the object
 means for utilizing said projection data and said mathematical modelling of the object in Bayesian inversion based on Bayes' formula $$p(x|m) = \frac{p_{pr}(x) p(m|x)}{p(m)}$$

the prior distribution $p_{pr}(x)$ representing mathematical modelling of the object, x representing the object image vector, which comprises values of the X-ray attenuation coefficient inside the object, m representing projection data, the likelihood distribution p(m|x) representing the X-radiation attenuation model between the object image vector x and projection data m, p(m) being a normalization constant and the posteriori distribution p(x|m) representing the three-dimensional information of the object, and
 means for producing three-dimensional medical X-ray imagine information of the object.

20. A medical x-ray device arrangement according to claim 19, characterized in that the three-dimensional information of the object is one or more two-dimensional images representing X-ray attenuation coefficient along slices through the object.

21. A medical x-ray device arrangement according to claim 19, characterized in that said medical X-ray imaging means for producing three-dimensional information produces three-dimensional information of the object that is a three-dimensional voxel representation of the X-ray attenuation in the object.

22. A medical X-ray device arrangement according to claim 19, characterized in that the medical X-ray device arrangement comprises means for modelling a measurement as $$m = Ax + e,$$

where matrix A contains the lengths of the path of the X-ray inside each voxel and the noise e is independent of object image vector x leading to the likelihood distribution $$p(m|x) = p_{noise}(m - Ax).$$

23. A medical X-ray device arrangement according to claim 19 characterized in that the medical X-ray device arrangement comprises means for modelling the object mathematically so that X-radiation attenuates when passing through the object, which means that every image voxel is nonnegative.

24. A medical X-ray device arrangement according to claim 19, characterized in that the medical X-ray device arrangement comprises means for modelling the object mathematically by the formula:

$$p_{pr}(x) = \exp\left(-\alpha \sum_N U_N(x)\right)$$

where the sum is taken over a collection of 3D neighbourhoods N and the value $U_N(x)$ depends only on the values of voxels belonging to the neighborhood N, and α is a positive regularization parameter used to tune the width of the prior distribution.

25. A medical x-ray device arrangement according to claim 19, characterized in that a 3D tomographic problem is divided into a stack of 2D tomographic problems, and for every such 2D problem, the medical X-ray device arrangement comprises means for modelling the object mathematically by the formula:

$$p_{pr}(x) = \exp\left(-\alpha \sum_N U_N(x)\right)$$

where the sum is taken over a collection of 2D neighbourhoods N and the $U_N(X)$ depends only on the values of pixels belonging to the neighborhood N, and α is a positive regularization parameter used to tune the width of the prior distribution, and the 2D tomographic problems are related to each other by the formula $$pr3D(x(j)) = \exp(-\gamma \Sigma\Sigma |x(j)[k,q] - x(j-1)[k,q]|),$$

where the sums are taken over all pixels (k1, . . . ,K, q=1, . . . ,Q) and γ>0 is another regularization parameter.

26. A medical X-ray device arrangement according to claim 25, characterized in that the neighborhoods comprise two neighboring pixels xj, xk or voxels xj, xk and $U_N(x)$ calculates a power of the $$p_{pr}(x^{(j)}) = \exp\left(-\alpha\left(\sum_{k=1}^{K-1}\sum_{q=1}^{Q} |x^{(j)}[k,q] - x^{(j)}[k+1,q]|^s + + \sum_{k=1}^{K}\sum_{q=1}^{Q-1} |x^{(j)}[k,q] - x^{(j)}[k,q+1]|^s\right)\right)$$

absolute value of the difference, leading to the formula where s is a positive real number and α is a regularization parameter used to tune the width of the prior distribution.

27. A medical X-ray device arrangement according to claim 26, characterized in that the medical X-ray device arrangement comprises means for modelling the object mathematically by setting s=1 corresponding to total variation (TV) distribution for prior describing objects comprising different regions with well-defined boundaries.

28. A medical X-ray device arrangement according to claim 19, characterized in that the medical X-ray device arrangement comprises means for modelling the object mathematically by assuming that mathematical modelling is qualitative structural information of the target where the structural information is encoded in prior distributions that are concentrated around image vectors x that correspond to the physiological structures of the target.

29. A medical X-ray device arrangement according to claim 19, characterized in that the medical X-ray device arrangement comprises means for modelling the object mathematically by assuming that mathematical modelling comprises a list of possible attenuation coefficient values in the object.

30. A medical X-ray device arrangement according to claim 19, characterized in that the medical X-ray device arrangement comprises means for modelling the object mathematically by assuming that the X-ray imaging geometry, such as X-ray source position, has unknown error modelled in the distribution p(m|x).

31. A medical X-ray device arrangement according to claim 19, characterized in that the medical X-ray device arrangement comprises means for modelling the object mathematically by assuming that X-radiation measurement noise is Poisson distributed.

32. A medical X-ray device arrangement according to claim 19, characterized in that the medical X-ray imaging is dental radiography.

33. A medical X-ray device arrangement according to claim 19, characterized in that the medical X-ray imaging is surgical C-arm imaging.

34. A medical X-ray device arrangement according to claim 19, characterized in that the medical X-ray imaging is mammography.

35. A medical X-ray device arrangement according to claim 19, characterized in that the medical X-ray device arrangement comprises means for producing three-dimensional information of the object on the basis of the maximum a posteriori estimator (MAP), which is calculated by the equation:

$$p(X_{MAP}|m) = \max p(x|m),$$

m representing projection data and x representing the object image vector and where the maximum on the right hand side of the equation is taken over all x.

36. A medical X-ray device arrangement according to claim 19, characterized in that the medical X-ray device arrangement comprises means for producing three-dimensional information of the object on the basis of the conditional mean estimator (CM), which is calculated by the equation $$X_{CM} = \int x p(x|m) dx$$

where m represents projection data and x represents the object image vector.

* * * * *